(12) United States Patent
Kim et al.

(10) Patent No.: US 11,814,171 B2
(45) Date of Patent: Nov. 14, 2023

(54) METHOD OF CONTROLLING DRONE INSIDE VEHICLE

(71) Applicants: HYUNDAI MOTOR COMPANY, Seoul (KR); KIA CORPORATION, Seoul (KR)

(72) Inventors: Ji Ah Kim, Seoul (KR); Jin Ho Hwang, Cheonan-si (KR); Min Ho Cho, Suwon-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 246 days.

(21) Appl. No.: 17/316,945

(22) Filed: May 11, 2021

(65) Prior Publication Data

US 2022/0063804 A1    Mar. 3, 2022

(30) Foreign Application Priority Data

Sep. 2, 2020    (KR) .......................... 10-2020-0111791

(51) Int. Cl.
*B64C 39/02*    (2023.01)
*B64D 1/16*    (2006.01)
(Continued)

(52) U.S. Cl.
CPC .............. *B64C 39/024* (2013.01); *A61L 2/24* (2013.01); *B60L 58/13* (2019.02); *B64D 1/16* (2013.01);
(Continued)

(58) Field of Classification Search
CPC ....... B64C 39/024; B64C 19/00; B64C 39/02; A61L 2/24; A61L 2202/25; A61L 2202/14; A61L 2202/16; A61L 2209/11; A61L 2/10; A61L 2/22; A61L 9/14; A61L 9/20; A61L 9/00; B60L 58/13; B60L 2200/10; B60L 2250/12; B60L 2250/22; B64D 1/16; B64D 1/22; G06Q 10/0832; G06Q 30/0265; B64U 50/19; B64U 80/86; B64U 2101/60; B64U 2201/104; B64U 2201/00; B64U 2101/00; B64U 30/20; B64U 2201/20; B64U 10/10;
(Continued)

(56) References Cited

U.S. PATENT DOCUMENTS 9,567,081 B1 * 2/2017 Beckman ................. B64D 1/10
11,465,578 B1 * 10/2022 Llamazares Domper ...................
B60R 21/055
(Continued)

FOREIGN PATENT DOCUMENTS

EP    3957562 A1 *   2/2022
JP    2018-165205 A   10/2018
(Continued)

*Primary Examiner* — Yonel Beaulieu
(74) *Attorney, Agent, or Firm* — LEMPIA SUMMERFIELD KATZ LLC

(57) ABSTRACT

A method of controlling a drone positioned in a vehicle includes: determining the initial condition of the drone positioned inside the vehicle, releasing locking of the drone upon receiving a user request from a vehicle controller, receiving vehicle state information from the vehicle controller by a drone controller, performing flight of the drone in response to the user request, and after completing the user request, returning the drone to an initial position thereof.

15 Claims, 4 Drawing Sheets

(51) Int. Cl.
*B64D 1/22* (2006.01)
*B60L 58/13* (2019.01)
*G06Q 10/0832* (2023.01)
*G06Q 30/0251* (2023.01)
*A61L 2/24* (2006.01)
*B64U 50/19* (2023.01)
*B64U 80/86* (2023.01)
*B64U 101/60* (2023.01)

(52) U.S. Cl.
CPC ........... *B64D 1/22* (2013.01); *G06Q 10/0832* (2013.01); *G06Q 30/0265* (2013.01); *A61L 2202/25* (2013.01); *B64U 50/19* (2023.01); *B64U 80/86* (2023.01); *B64U 2101/60* (2023.01); *B64U 2201/104* (2023.01)

(58) Field of Classification Search
CPC ...... Y02T 10/70; G05D 1/101; G05D 1/0011; G05D 1/027; G05D 1/00; G06F 21/44; G08B 21/182; G09F 21/08; H02J 7/0048
See application file for complete search history.

(56) References Cited

U.S. PATENT DOCUMENTS

| | | | |
|---|---|---|---|
| 11,526,861 B1 * | 12/2022 | Goetz | G05D 1/0022 |
| 2019/0023392 A1 * | 1/2019 | Micros | B64C 33/025 |
| 2020/0114836 A1 * | 4/2020 | Day | F16M 11/28 |
| 2021/0116942 A1 * | 4/2021 | Gandiga | B64C 39/024 |
| 2022/0215337 A1 * | 7/2022 | Li | G06Q 50/30 |

FOREIGN PATENT DOCUMENTS

| | | | |
|---|---|---|---|
| KR | 10-1860938 B1 | 5/2018 | |
| KR | 10-1901053 B1 | 9/2018 | |
| KR | 10-1981105 B1 | 5/2019 | |
| WO | WO-2016188955 A1 * | 12/2016 | B25J 9/00 |

* cited by examiner

METHOD OF CONTROLLING DRONE INSIDE VEHICLE

CROSS-REFERENCE TO RELATED APPLICATION

This application claims priority to and the benefit of Korean Patent Application No. 10-2020-0111791, filed on Sep. 2, 2020, the entire contents of which are incorporated herein by reference.

FIELD

The present disclosure relates to a method of controlling a drone positioned inside a vehicle, and more particularly to a method of controlling a drone positioned inside a vehicle for setting and controlling a flight path of the drone having various uses according to a user request inside the vehicle.

BACKGROUND

The statements in this section merely provide background information related to the present disclosure and may not constitute prior art.

In general, a drone is an aircraft that is wirelessly controlled by an operator, in early days, drones were developed for and used by the military, but recently have come to be used across a wide range of transport, leisure, and industry.

Thus, in accordance with current trends, drones have been used to prevent insufficient progresses for a long time with insufficient labor in a wide area during pest control such as spreading of pesticides and fertilizers in primary industries such as agriculture, fisheries, and livestock, and pest control using drones has drawn attention as the most realistic and efficient system to resolve problems of manpower shortage and costs in primary industries.

In accordance with current trends, drones have also come to be used in technological fields that use sterilization to prevent epidemics as well as pest control and spreading work, and technology using drones in various ways is currently developed.

Recently, technologies for improving a driving environment of a vehicle using a drone positioned near a vehicle have been developed, and technologies for unmanned flight of drones have been developed.

However, we have discovered that a drone is positioned outside a vehicle and receives information related to driving of the vehicle, and thus there is no configuration for managing a drone inside the vehicle. In addition, a drone may be positioned inside a vehicle to transfer an item to an appropriate position in response to a user request or to perform indoor disinfection based on whether an occupant is present.

SUMMARY

In one aspect, the present disclosure provides a control method for transferring an item in response to a request of an occupant using a drone positioned inside a vehicle.

In another aspect, the present disclosure provides a drone for automatically executing sterilization logic inside the vehicle with regard to an unmanned vehicle or a shared vehicle.

The objects of the present disclosure are not limited to the objects mentioned above, and other unmentioned objects will be understood by those skilled in the art from the following description, and will be more clearly appreciated through exemplary forms of the present disclosure. In addition, the object of the present disclosure may be realized by devices disclosed in the claims and combinations thereof.

The method of controlling the drone positioned inside the vehicle for achieving the aforementioned objects of the present disclosure may have the following configuration.

In one form, a method of controlling a drone positioned inside a vehicle includes: determining an initial condition of the drone positioned inside the vehicle, releasing locking of the drone upon receiving a user request by a vehicle controller, receiving vehicle state information from the vehicle controller by a drone controller, performing flight of the drone in response to the user request, and after completing the user request, returning the drone to an initial position inside the vehicle.

The determining the initial condition of the drone may include determining whether a state of charge (SoC) of the drone is equal to or greater than a reference value. In another form, releasing locking of the drone may comprise: in response to determining that the SoC of the drone is equal to or greater than the reference value, releasing locking of the drone; and in response to determining that the SoC of the drone is less than the reference value, displaying a notification, indicating that the drone is not capable of flying, through a notice unit.

The receiving the vehicle state information may further include receiving information associated with the vehicle using a global positioning system (GPS), a navigation device, and a portable terminal positioned inside the vehicle. In particular, the information includes at least one of a position, a speed, a yaw rate, a pitch, roll data, or driving direction data of the vehicle.

The method may further include receiving at least one of the position information, the speed, the yaw rate, pitch, and roll data of the vehicle, or the driving data of the vehicle using the GPS, the navigation device, and the portable terminal positioned inside the vehicle, receiving GPS information of the vehicle, establishing a connection with the navigation device when reception of the GPS information of the vehicle fails, receiving the position information of the vehicle using the portable terminal when the connection with the navigation device fails, and receiving the yaw rate, pitch, and roll data of the vehicle and compensating for vehicle state information received in the receiving by the drone controller.

The receiving the vehicle state information may further include setting a flight path in response to the user request by the drone controller.

The performing flight of the drone in response to the user request may further include displaying an advertisement through swiveling of the drone inside the vehicle.

The performing flight of the flight in response to the user request may include picking up an item corresponding to the user request, and transferring the picked-up item to a holder requested by a user.

The transferring the picked-up item to the holder requested by the user may include activating an electromagnet of a holder to correspond to magnetism positioned below the item, and when the item is positioned in the holder, deactivating the electromagnet of the holder by the vehicle controller.

The activating the electromagnet of the holder to correspond to the magnetism positioned below the item may further include, when the electromagnet is not activated, displaying a notification indicating that the item is not capable of being transferred to the occupant through a notice unit.

The performing flight of the drone in response to the user request may include determining whether an occupant is present, and executing a sterilization logic through the drone when no occupant is present.

The performing flight of the drone in response to the user request may include measuring whether an obstacle is present on a flight path of the drone in real time, through a sensor unit.

The performing flight of the drone in response to the user request may include receiving information on an interior space of the vehicle through a radar device positioned in the drone, and compensating for a flight path in real time using at least one of a vision sensor or a temperature sensor positioned in the drone.

The compensating for the flight path using at least one of the vision sensor or the temperature sensor may include determining whether the vision sensor and the temperature sensor fail, and displaying a notification indicating unavailability of service through a notice unit when all of the radar device, the vision sensor, and the temperature sensor fail.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 4:
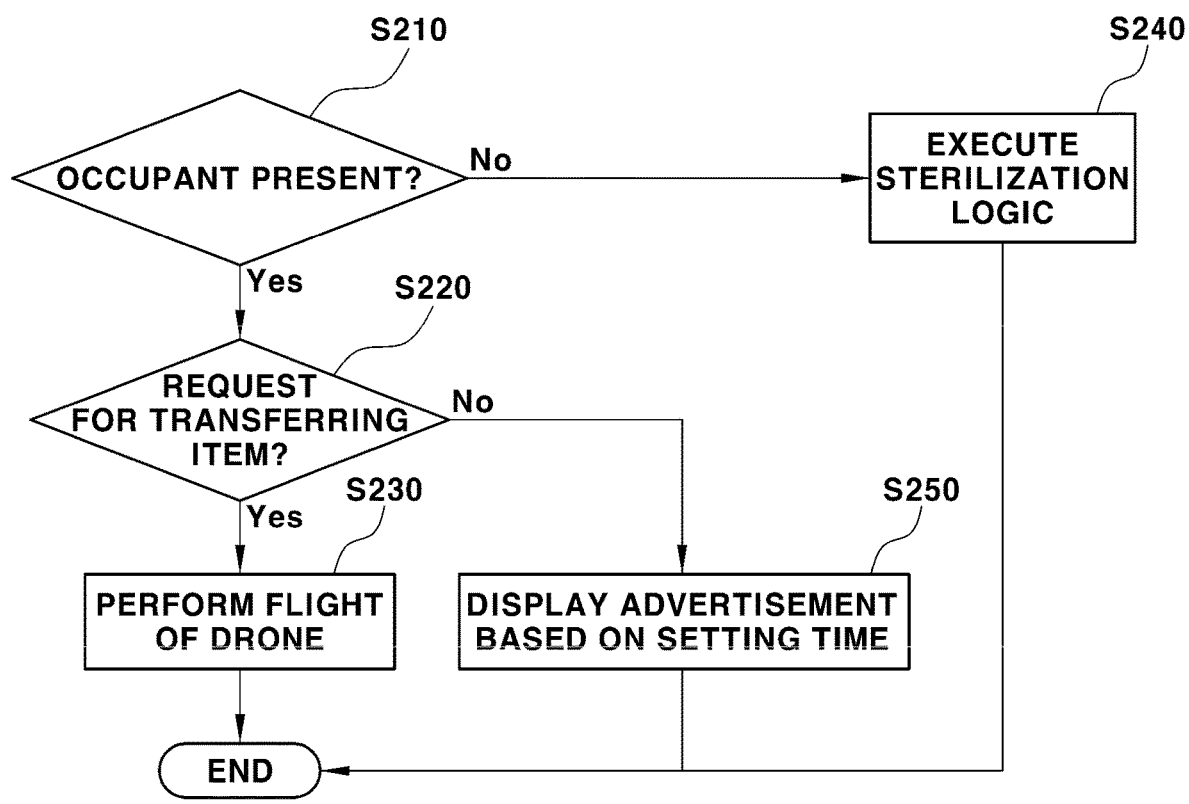
Figure 5:
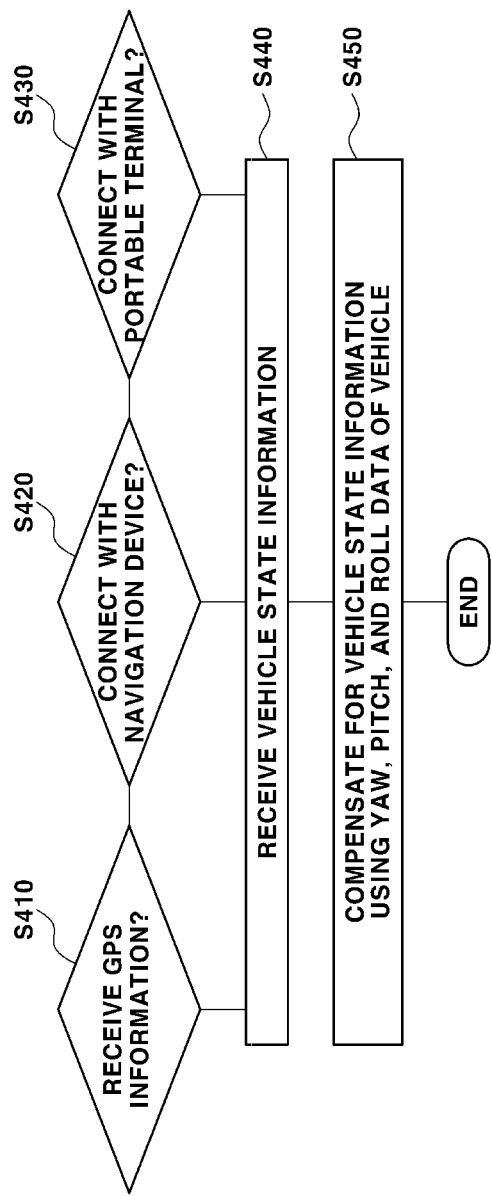

FIG. 4 is a flowchart of driving of a drone in response to a user request of a method of controlling a drone positioned inside a vehicle according to an exemplary form of the present disclosure; and FIG. 5 is a flowchart showing an operation of receiving vehicle state information of a method of controlling a drone positioned inside a vehicle according to an exemplary form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Reference will now be made in detail to example forms, examples of which are illustrated in the accompanying drawings. Exemplary forms are modified in various forms and are not limited to the forms illustrated hereinafter. The forms herein are rather introduced to provide easy and complete understanding of the scope and spirit of example forms.

In the present specification, it should be understood that the terms, such as "unit", "sensor", "drone", or "logic" described in the specification should be understood as a unit that processes at least one function or operation and that may be embodied in a hardware manner, a software manner, or a combination of the hardware manner and the software manner.

Hereinafter, the present disclosure will be described in detail by explaining exemplary forms of the present disclosure with reference to the attached drawings, the same or corresponding numerals in the drawings denote the same or corresponding elements, and thus their description will be omitted.

Hereinafter, the term "fail" described in the specification may be interpreted as including any case in which a component is not capable of performing a function thereof due to a malfunction of hardware or software.

Hereinafter, the term "drone" described in the specification may be interpreted as an unmanned aircraft that is capable of being moved along a flight path or performing hovering by driving at least one propeller.

The present disclosure relates to a method of controlling a drone 200 positioned inside a vehicle 100 and configured to fly inside the vehicle 100 in response to a user request, and more particularly to technology of receiving and controlling data for performing flight of the drone 200 coupled to a ceiling of the vehicle 100 and to perform wireless charging.

Figure 1:
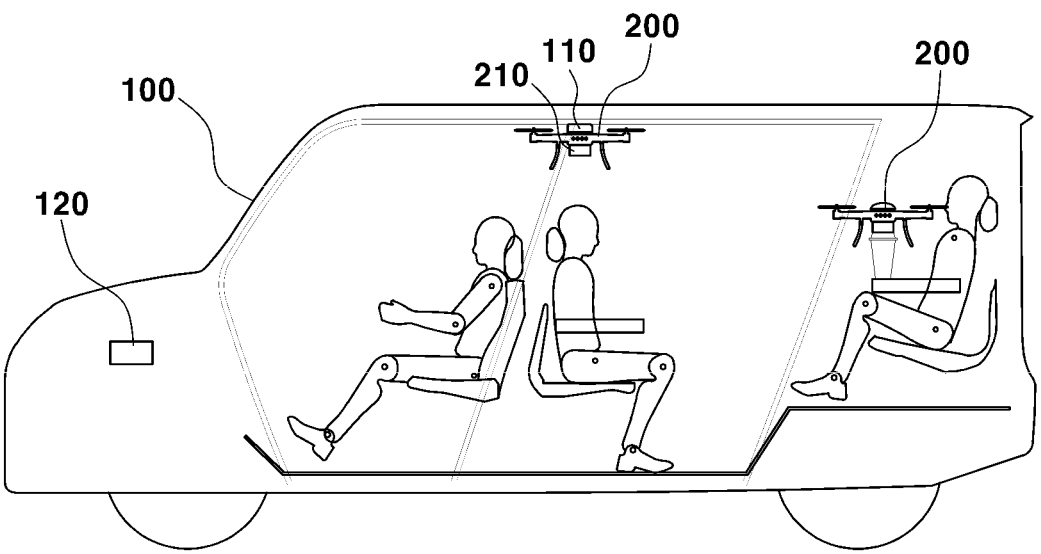
FIG. 1 is a side cross-sectional view of a vehicle including a device for controlling a drone inside a vehicle according to an exemplary form of the present disclosure.
Figure 2:
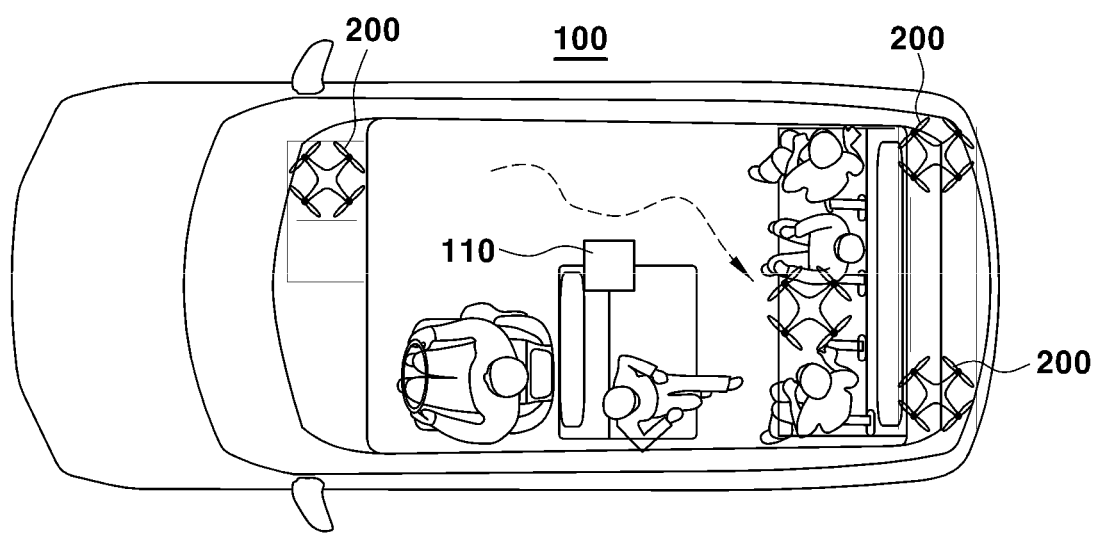
FIG. 2 is a diagram showing an upper surface of a vehicle including a device for controlling a drone inside a vehicle according to an exemplary form of the present disclosure.

FIGS. 1 and 2 are diagrams showing a drone positioned inside a vehicle and arrangement of the inside of the vehicle including the drone according to an exemplary form of the present disclosure.

As shown in the drawings, the drone 200 may be fixedly positioned in an interior space of the vehicle 100, and thus, the drone in one form may be positioned to be coupled to a station 110 positioned at a ceiling of the vehicle 100. According to another form of the present disclosure, the drone 200 may be positioned to be coupled to the station 110 formed at various positions such as a front head lining or a front ceiling panel of the vehicle 100.

The drone 200 may be positioned at the station 110 in an initial condition or in the state in which a user request is not applied. The station 110 may include a charging module for wirelessly charging the drone 200, and thus may be configured to wirelessly charge the drone 200 when coupled to the station 110.

The charging module for performing wireless charging may be capable of charging a battery of the drone 200 using an electromagnetic inductive coupling method, which is a method of transferring power between a primary coil positioned in the charging module and a secondary coil coupled to a battery of the drone 200. When a magnet is moved around a coil, induced current may be generated to thereby generate electricity. That is, a transmitter generates a magnetic field and a receiver generates energy instead of a function of the magnet. A phenomenon in which current is generated using a coil and a magnet is referred to as a self-inductance effect, and is advantageous in that energy transfer efficiency is excellent.

The next power transfer method is a method using resonance for wirelessly transferring power using the principle of resonance power transfer even if a target is spaced apart from a charging device by several meters. The method uses resonance, which is a physical phenomenon in which, when a tuning fork is struck, a wine glass next to the tuning fork rings at the same frequency as the tuning fork, and similarly, power is wirelessly transferred to a battery of the drone 200 via resonance of an electromagnetic wave containing electric energy instead of a resonant sound wave.

The last wireless power transfer method is a method of wirelessly transferring power through radiation of radio waves (RF/micro wave radiation), which is a new concept of a power transfer method of converting power energy into microwave advantageous for wireless transfer and transferring energy.

The drone 200 may wirelessly communicate with a vehicle controller 120 through a drone controller 210 positioned inside the drone 200, and may be configured to receive vehicle state data and/or vehicle behavior data received by the vehicle controller 120 and to transmit and receive information on a flight path of the drone 200 and real-time information on the state of the drone 200 to and from the vehicle controller 120 through the drone controller 210. The drone controller 210 and the vehicle controller 120 may perform wireless communication using a short-distance communication module such as Bluetooth or NFC, but the present disclosure is not limited thereto. According to another form of the present disclosure, the drone controller 210 may be configured to receive vehicle state information, position information of the vehicle 100, and speed information of the vehicle 100 through a network, and may be configured to communicate with a portable terminal through at least one of LAN, WLAN, PSTN, or a cellular phone network.

The vehicle controller 120 may be configured to receive position data of the vehicle 100, speed data of the vehicle 100, driving data of the vehicle 100, and so on in conjunction with a global positioning system (GPS), a navigation device, or the like of the vehicle 100. In addition, the vehicle controller 120 may be configured to receive driving behavior data of the vehicle 100 through a plurality of sensors positioned in the vehicle 100, and thus may receive a yaw rate, a pitch, and roll data of the vehicle 100 as driving behavior data of the vehicle 100. In more detail, the vehicle controller 120 or the drone controller 210 may be configured to receive at least one of the position, speed, driving behavior, yaw rate, pitch, or roll data of the vehicle 100.

That is, the drone controller 210 may be configured to receive vehicle state information through the vehicle controller 120 to maintain the drone 200 in a horizontal state based on the inside of the vehicle 100 and to simultaneously receive at least one data of a yaw rate, a pitch, or roll data as behavior data of the vehicle 100. The drone controller 210 may be configured to compensate for a flight path of the drone 200 by compensating for the vehicle state information using the received vehicle behavior data.

The drone controller 210 may be configured to control output of the drone 200 to perform flight of the drone 200 parallel to the inside of the vehicle 100 based on the vehicle state data and the vehicle behavior data.

The vehicle controller 120 may be configured to receive a user request using an application that uses a switch or a portable terminal positioned inside the vehicle 100. According to one form of the present disclosure, the user request may include a request for transfer of an item positioned inside the vehicle 100, execution of sterilization logic to sterilize the vehicle 100, displaying an advertisement inside the vehicle 100 through swiveling of the drone 200, or the like.

The vehicle controller 120 may be configured, upon receiving such a user request, to transmit the user request to the drone controller 210, to release locking between the drone 200 and the station 110, and to perform flight of the drone 200. In more detail, when receiving the user request, the drone 200 according to the present disclosure may be configured to determine the initial condition of the drone 200, and thus may be configured to determine, in advance, whether a state of charge (SoC) of a battery of the drone 200 is equal to or greater than a reference value, and to display information indicating that flight is impossible on a notice unit when the SoC of the battery of the drone 200 is less than the reference value. The notice unit may be positioned on the drone 200 or may be positioned inside the vehicle 100, and in more detail, may be positioned on a switch or a display for inputting the user request.

When the SoC of the battery of the drone 200 is equal to or greater than the reference value, the drone controller 210 may be configured to receive vehicle state information in order to set a flight path of the drone 200 when receiving a user request. According to one form of the present disclosure, the vehicle state information may include the driving direction, speed, position, yaw rate, pitch, and roll data of the vehicle 100, or the like. In detail, the vehicle controller 120 may be configured to transmit information on the speed and acceleration of the vehicle 100, measured through a GPS, a navigation device, and an APS sensor positioned in the vehicle 100, to the drone controller 210. The vehicle controller 120 or the drone controller 210 may be configured to receive vehicle state information from a portable terminal through wireless communication. In addition, the drone controller 210 may be configured to receive the yaw rate, pitch, and roll data of the vehicle 100 and to compensate for the received vehicle state based thereon, and thus may be configured to set a flight path of the drone 200 and an output value of each propeller positioned in the drone 200 depending on a vehicle behavior.

That is, for flight of the drone 200, the drone controller 210 may be configured to receive vehicle state information to position the drone 200 inside the vehicle 100 depending on the driving state of the vehicle 100 and to set a flight path based on the received vehicle state information. Because it is difficult to set a horizontal and vertical flight path of the drone 200 based only on position information of the vehicle 100, the drone controller 210 may be configured to compensate for the vehicle state information received by the drone controller 210 based on the yaw, pitch, and roll data measured through a sensor unit (not shown) of the vehicle 100. The drone controller 210 may be controlled to have the horizontal and vertical flight path of the drone 200 and a flight speed corresponding to the driving state of the vehicle 100 based on the compensated vehicle state information.

The drone controller 210 may be configured to receive the vehicle state information and to set the flight path of the drone 200, and thus may be configured to scan the structure of the inside of the vehicle 100 through a plurality of sensor units (not shown) positioned in the drone 200. The drone 200 may be configured to measure an obstacle in real time using at least one of a vision sensor or a temperature sensor while flying in the interior space of the vehicle 100. In detail, the drone 200 may be configured to scan the interior space of the vehicle 100 using a radar device, and during flight, may be configured to measure changes in the space in real time using at least one of a radar device, a vision sensor, or a temperature sensor, and to compensate for a flight path based on the measured change.

As such, the drone controller 210 may be configured to set a first flight path in an interior space of the vehicle 100 and to measure a change in the interior environment of the vehicle 100 in real time through a plurality of sensor units while the drone 200 moves along the set flight path, and thus the drone controller 210 may be configured to compensate for the flight path of the drone 200 in real time.

The drone controller 210 and the vehicle controller 120 may be operatively associated with each other to determine whether the current state is a state in which the drone 200 is capable of flying, and may be configured to set the flight path of the drone 200, to set horizontal and vertical-direction position information of the drone 200 for flight of the drone 200, and to perform flight in response to a user request.

Figure 3:
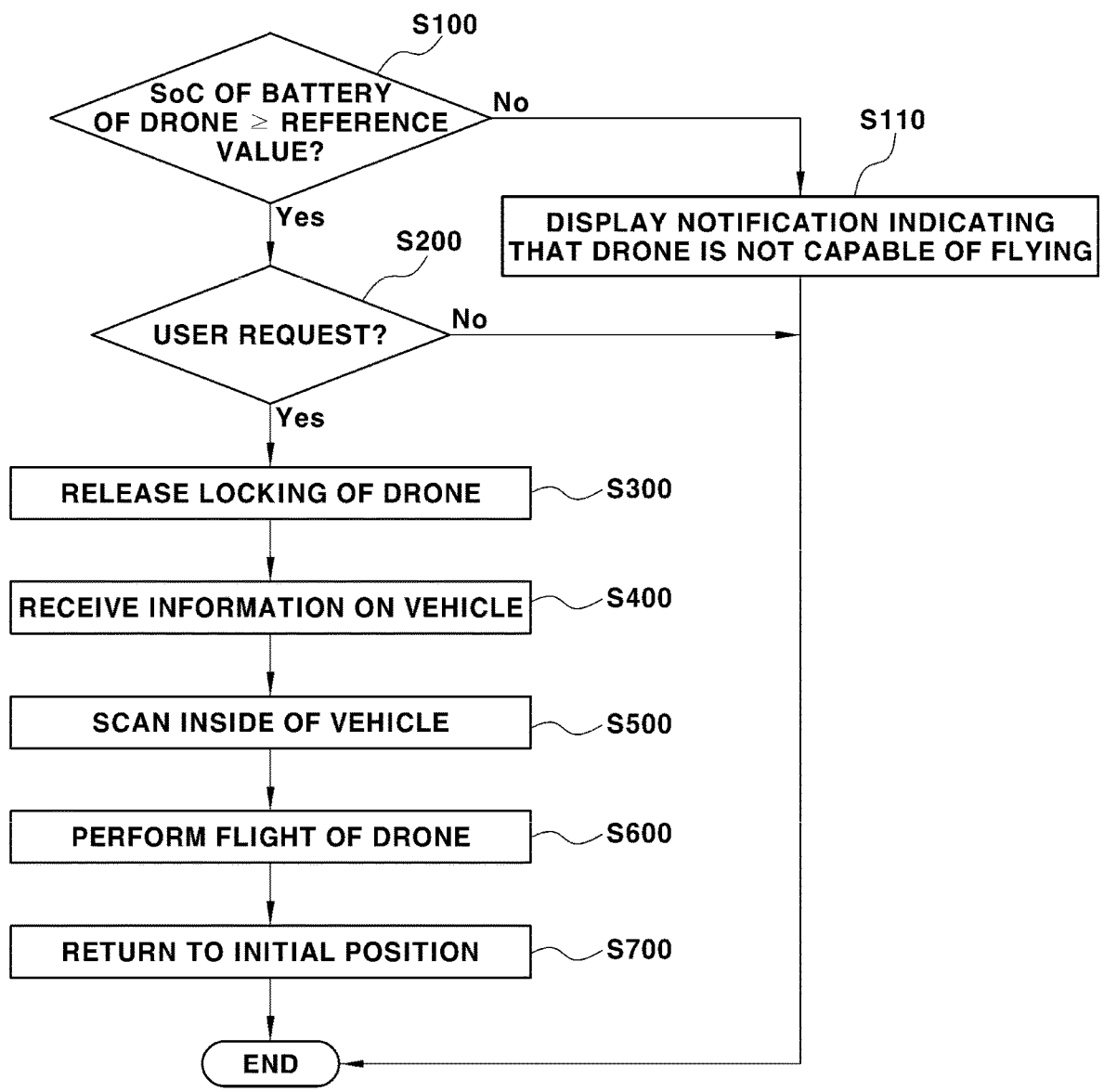
FIG. 3 is a flowchart of a method of controlling a drone positioned inside a vehicle according to an exemplary form of the present disclosure.

FIG. 3 is a flowchart of a method of the drone 200 positioned inside the vehicle 100 according to another form of the present disclosure.

As shown in the drawing, a first operation of determining the initial condition of the drone 200 may be performed, in which case whether a state of charge (SoC) of a battery of the drone 200 is equal to or greater than a referenced value stored in the drone controller 210 or the vehicle controller 120 may be determined (at step S100). When the SoC of the battery of the drone 200 is less than the reference value, notification indicating that the drone 200 is not capable of flying may be transmitted through a notice unit (at step S110), and when the SoC of the battery of the drone 200 is equal to or greater than the reference value, whether a user request signal is applied may be determined (at step S200).

The user request signal may be applied through the vehicle controller 120 prior to an operation of determining the initial condition of the drone 200, and when the user request is applied through the vehicle controller 120, the user request signal may be transmitted to the drone controller 210, and whether the initial condition of the drone 200 is satisfied may be determined.

That is, when the user request signal is applied to the vehicle controller 120, the drone controller 210 may be configured to determine the initial condition of the drone 200, and after the initial condition of the drone 200 is satisfied, the user request signal may be applied to the drone controller 210 from the vehicle controller 120, and setting of a flight path may be performed in response to the corresponding request.

When the drone controller 210 determines that the initial condition of the drone 200 is satisfied and the user request signal is applied, the vehicle controller 120 may control the station 110 to release locking of the drone 200 (at step S300) and may receive information on the vehicle 100 from the drone controller 210 (at step S400).

The drone controller 210 may be configured to receive vehicle state information (information on the vehicle 100) from the vehicle controller 120, and thus may be configured to receive position information, speed, a driving path, and a current driving direction of the vehicle 100 using a navigation device, a GPS, or a plurality of sensor units positioned in the vehicle 100, or the like. In addition, the drone controller 210 may be configured to receive current behavior state information of the vehicle 100 from the vehicle controller 120, and thus may be configured to receive the yaw rate, pitch, and roll data of the vehicle 100. In more detail, the vehicle controller 120 or the drone controller 210 may be operatively associated with a portable terminal of a user, and thus may be configured to receive vehicle state information using the portable terminal and to control the drone 200 in a horizontal or vertical direction.

As described above, the drone controller 210 may be configured to receive vehicle state data and behavior information of the vehicle 100 and to set the flight path of the drone 200, and thus may control the drone 200 to perform flight of the drone 200 in a horizontal state along the inside of the vehicle 100 that is traveling.

After receiving information on the vehicle 100, the drone controller 210 may be configured to scan the inside of the vehicle 100 through a sensor unit positioned in the drone 200 (at step S500). The operation of scanning the inside of the vehicle 100 may include an operation of determining the shape of the inside of the vehicle 100 and an obstacle through a radar device positioned in the drone 200. That is, an occupant and an obstacle in an interior space of the vehicle 100 may be determined through a radar device, and a flight path of the drone 200 may be set.

After locking of the drone 200 is released from the station 110, the drone controller 210 may be configured to control output of the drone 200 in horizontal and vertical directions to correspond to the inside of the vehicle 100 based on vehicle state information and may be configured to move the drone 200 along a flight path in response to a user request (at step S600).

After the drone 200 performs flight to complete the user request, the drone 200 may be configured to switch to the state in which the drone 200 is docked on the station 110 and to return to the station 110 (at step S700).

As such, according to the present disclosure, a flight path may be set by scanning the interior structure of the vehicle 100, and the drone 200 may be controlled through the drone controller 210 to perform flight in response to the user request and to then return to an original position.

FIG. 4 is a flowchart of a method of the drone 200 positioned inside the vehicle 100 in response to a user request.

According to another form of the present disclosure, the user request may include a request for transferring an item in response to a request of an occupant, and a logic for performing sterilization of the inside of the vehicle 100 and a display operation of displaying an image set by moving the drone inside the vehicle 100 within a predetermined time when an occupant is not present.

That is, first, whether an occupant is present may be determined through the vehicle controller 120 (at step S210). When an occupant is present, whether there is a request for transferring an item of an occupant may be determined (at step S220), and when the request for transferring an item is applied, flight of the drone 200 may be performed (at step S230).

According to another form of the present disclosure, in order to perform flight of the drone 200 for transferring an item, the vehicle 100 may contain an item storage place from which an item is picked up by the drone 200, and the drone controller 210 may be configured to determine the position of an item depending on each item. In detail, the drone 200 may be configured to classify items through a radar device, and the drone controller 210 may be configured to receive information on the respective positions of the items and the remaining amounts of the items from the vehicle controller 120 and to set a flight path of the drone 200.

The drone 200, having picked up an item, may fly to position the item in a holder adjacent to a user in response to the user request, and thus may be controlled to position the item at a predetermined position along a path provided from the drone controller 210. In more detail, the drone controller 210 may perform control to release a fixing unit for coupling between the drone 200 and an item in order to position the item in the holder of the vehicle 100. The vehicle controller 120 may be configured to activate an electromagnet positioned inside the holder and to configure attraction between the electromagnet and a magnet material positioned below the item. Accordingly, the vehicle controller 120 may be configured to fixedly fix the item inside the holder.

When determining that fixation between the item and the drone 200 is released and the item is positioned inside the holder, the vehicle controller 120 may be configured to deactivate the electromagnet inside the holder.

In addition, when the electromagnet positioned inside the holder is not activated, the vehicle controller 120 may be configured to display a notification indicating that the item is not capable of being transferred because the electromagnet is not capable of being activated, through a notice unit, and thus the vehicle controller 120 may provide a notification prompting a user to manually remove the item positioned at the fixing unit.

In addition, when the drone 200 is moved to a position adjacent to the user, the drone controller 210 may be configured to compensate for a flight path in real time to avoid colliding with the user using at least one of a vision sensor or a temperature sensor.

The drone controller 210 may determine failure of the vision sensor or the temperature sensor of the drone 200 during flight of the drone 200, and thus may determine failure of each sensor by comparing data of the vision sensor or the temperature sensor, measured based on the flight path, through a radar device. According to one form of the present disclosure, when an abnormality occurs in terms of a change from a seat along a path or a change between the drone 200 and an immobile component through the vision sensor of the drone 200, the drone controller 210 may determine failure of the vision sensor, and when there is no temperature change value or a data reception error occurs, the drone controller 210 may determine that the temperature sensor has failed. However, failure of the vision sensor or failure of the temperature sensor may include any case in which functions of sensors are degraded in terms of hardware or software.

When all of the radar device, the vision sensor, and the temperature sensor are in a failed state, the drone controller 210 may be configured to determine that the drone 200 is incapable of flying and to display a notification indicating unavailability of service through a notice unit. That is, the drone controller 210 may determine abnormality of driving of the radar device or abnormality of data based on pre-stored data obtained by scanning the inside of the vehicle 100, and may determine abnormality of measurement of the vision sensor or the temperature sensor, and thus when a sensor required to perform flight is abnormal, the drone controller 210 may be configured to display a notification indicating unavailability of service.

The method may include operation S250 of displaying an advertisement based on a pre-input setting time by the drone controller 210 when there is no request for transferring an item even if an occupant is present.

In contrast, the method may include an operation of performing sterilization logic to perform sterilization by spraying a disinfectant positioned in the drone 200 or emitting UV light at step S240. The sterilization logic according to the present disclosure may refer to control for deploying the drone 200 along a set flight path.

That is, in the operation of performing the sterilization logic, the drone controller 210 may be configured to scan an interior space of the vehicle 100 through a radar device, to perform flight of the drone 200 to a position adjacent to a seat, a ceiling, and a floor, and to perform sterilization of the inside of the vehicle 100 by spraying a disinfectant or emitting UV light.

As such, the present disclosure relates to a method of controlling the drone 200 according to whether an occupant is present, and the control method of setting a flight path of the drone 200 and compensating for the flight path in real time in response to each user request has been described.

FIG. 5 is a flowchart of an operation of receiving vehicle state information, that is, a method of receiving at least one of position information, speed information, or driving direction information of the vehicle 100 using a controller of the vehicle 100, a GPS, a navigation device, and a portable terminal positioned in the vehicle 100 and a method of receiving yaw, pitch, and roll data of the vehicle 100, which is behavior of the vehicle 100, as a lower form of vehicle state information.

As shown in the drawing, the drone controller 210 may be configured to receive at least one of position information, speed information, yaw rate, pitch, and roll data, or driving direction data of the vehicle 100 using a controller of the vehicle 100, a GPS, a navigation device, and a portable terminal positioned in the vehicle 100. In detail, the controller of the vehicle 100 may receive GPS information of the vehicle 100 (at step S410), when reception of GPS information fails, the controller of the vehicle 100 may be operatively associated with the navigation device (at step S420), and when a connection between the GPS information and the navigation device fails, the controller of the vehicle 100 may be operatively associated with the portable terminal (at step S430).

According to one form of the present disclosure, as described above, the drone controller 210 may sequentially determine whether the controller of the vehicle 100 is operatively associated with the GPS, the navigation device, or the portable terminal of the vehicle 100, which are targets for receiving state information of the vehicle 100. According to another form of the present, the drone controller 210 may be configured to simultaneously use the GPS, the navigation device, and the portable terminal positioned in the vehicle 100 to receive at least one of speed information, position information, or driving direction data of the vehicle 100 (at step S440).

The drone controller 210 may be configured to receive the yaw rate, pitch, and roll data, measured through the sensor unit of the vehicle 100, and to compensate for the received vehicle state information based on the speed information, the position information, and the driving direction data of the vehicle 100 (at step S450).

That is, the drone controller 210 may be configured to control the angle at which the drone 20 is inclined and the output applied to each propeller based on the position, speed, and driving direction data of the vehicle 100, and thus may be configured to set horizontal and vertical directions of the drone 200 using the yaw rate, pitch, and roll data as behavior information of the vehicle 100. Thus, the drone controller 210 may be configured to compensate for a horizontal flight condition of the drone 200 according to the yaw rate, pitch, and roll data as the current behavior information of the vehicle 100 based on driving environment information of the vehicle 100, and thus may be configured to perform flight of the drone 200 in horizontal and vertical directions in response to a behavior of the inside of the vehicle 100.

As such, the present disclosure relates to a method of controlling the flight of the drone 200 positioned inside the vehicle 100 and may provide a method of controlling the drone 200 positioned inside the vehicle 100 to set a flight path of the drone controller 210 in response to a user request and compensating for the path in real time while the drone 200 flies.

The present disclosure may have the following effects based on the combination and usage relationships of the present form and the aforementioned configuration.

The present disclosure may have an effect of improving the convenience of an occupant by controlling a drone positioned inside a vehicle.

In addition, the present disclosure may have an effect of providing excellent ride comport through a method of controlling a drone for automatically disinfecting and sterilizing a shared vehicle.

The detailed description is used to exemplify the present disclosure. The description herein is given to show exemplary forms of the present disclosure, and the present disclosure may be used in various other combinations, changes, and environments. That is, the present disclosure may be changed or modified within the scope of the concept of the present disclosure disclosed in the specification, the equivalent scope of the given disclosure, and/or the scope of the technology or knowledge in the art. The described form is the ideal form for implementing the technological spirit of the present disclosure, but may be changed in various forms within the sprit and scope of the present disclosure. Thus, the detailed description of the present disclosure herein is merely exemplary, and is not intended to limit the present disclosure.

What is claimed is:

1. A method of controlling a drone positioned inside a vehicle, the method comprising:
    determining an initial condition of the drone positioned inside the vehicle;
    releasing, by a vehicle controller, locking of the drone upon receiving a user request;
    receiving, by a drone controller, vehicle state information from the vehicle controller;
    performing flight of the drone in response to the user request; and
    after completing the user request, returning the drone to an initial position inside the vehicle,
    wherein performing flight of the drone in response to the user request comprises:
        receiving information on an interior space of the vehicle through a radar device positioned in the drone; and
        compensating for a flight path of the drone in real time using at least one of a vision sensor or a temperature sensor positioned in the drone.

2. The method of claim 1, wherein determining initial condition of the drone comprises:
    determining whether a state of charge (SoC) of the drone is equal to or greater than a reference value.

3. The method of claim 2, wherein releasing locking of the drone comprises:
    in response to determining that the SoC of the drone is equal to or greater than the reference value, releasing locking of the drone; and
    in response to determining that the SoC of the drone is less than the reference value, displaying, by a notice unit, a notification indicating that the drone is not capable of flying.

4. The method of claim 1, wherein receiving the vehicle state information further comprises:
    receiving information associated with the vehicle using a global positioning system (GPS), a navigation device, and a portable terminal positioned inside the vehicle, wherein the information includes at least one of a position, a speed, a yaw rate, a pitch, roll data, or driving direction data of the vehicle.

5. The method of claim 4, further comprising:
    receiving GPS information of the vehicle;
    in response to a failure to receive the GPS information, establishing a connection with the navigation device;
    in response to a failure to establish the connection with the navigation device, receiving the position of the vehicle using the portable terminal; and
    receiving the yaw rate, pitch, and roll data of the vehicle and compensating for the vehicle state information received by the drone controller.

6. The method of claim 1, wherein receiving the vehicle state information further comprises setting a flight path in response to the user request by the drone controller.

7. The method of claim 1, wherein performing flight of the drone in response to the user request further comprises displaying an advertisement through swiveling of the drone inside the vehicle.

8. The method of claim 1, wherein performing flight of the drone in response to the user request comprises:
    picking up an item corresponding to the user request; and
    transferring the picked-up item to a holder requested by a user.

9. The method of claim 8, wherein transferring the picked-up item to the holder requested by the user comprises:
    activating an electromagnet of the holder to correspond to magnetism positioned below the picked-up item; and
    in response to determining that the picked-up item is positioned in the holder, deactivating the electromagnet of the holder by the vehicle controller.

10. The method of claim 9, wherein activating the electromagnet of the holder further comprises:
    in response to determining that the electromagnet is not activated, displaying, by a notice unit, a notification indicating that the picked-up item is not capable of being transferred to an occupant of the vehicle.

11. The method of claim 1, wherein performing flight of the drone in response to the user request comprises:
    determining whether an occupant is present in the vehicle; and
    in response to determining that no occupant is present in the vehicle, executing a sterilization logic through the drone.

12. The method of claim 1, wherein performing flight of the drone in response to the user request comprises:
    measuring, by a sensor, whether an obstacle is present on a flight path of the drone in real time.

13. The method of claim 1, wherein compensating for the flight path in real time comprises:
    determining whether the vision sensor and the temperature sensor fail; and
    in response to determining that all of the radar device, the vision sensor, and the temperature sensor fail, displaying a notification indicating unavailability of service through a notice unit.

14. A method of controlling a drone positioned inside a vehicle, the method comprising:
    determining an initial condition of the drone positioned inside the vehicle;
    releasing, by a vehicle controller, locking of the drone upon receiving a user request;
    receiving, by a drone controller, vehicle state information from the vehicle controller;
    performing flight of the drone in response to the user request; and after completing the user request, returning the drone to an initial position inside the vehicle, wherein performing flight of the drone in response to the user request comprises displaying an advertisement through swiveling of the drone inside the vehicle.

15. A method of controlling a drone positioned inside a vehicle, the method comprising:

determining an initial condition of the drone positioned inside the vehicle;

releasing, by a vehicle controller, locking of the drone upon receiving a user request;

receiving, by a drone controller, vehicle state information from the vehicle controller;

performing flight of the drone in response to the user request; and after completing the user request, returning the drone to an initial position inside the vehicle, wherein performing flight of the drone in response to the user request comprises:

picking up an item corresponding to the user request; and transferring the picked-up item to a holder requested by a user.

\* \* \* \* \*